United States Patent [19]

Faltejsek et al.

[11] Patent Number: 4,738,930
[45] Date of Patent: Apr. 19, 1988

[54] APPARATUS FOR CONTINUOUSLY RECOVERING ETHANOL FROM FERMENTABLE SUGAR SOLUTIONS

[75] Inventors: Karl Faltejsek; Vilim Cvitas, both of Linz; Reinhart Hanke; Gottfried Klinar, both of Leoben, all of Austria

[73] Assignee: Voest-Alpine Aktiengesellschaft, Linz, Austria

[21] Appl. No.: 1,640

[22] PCT Filed: Apr. 9, 1986

[86] PCT No.: PCT/AT86/00030

§ 371 Date: Dec. 4, 1986

§ 102(e) Date: Dec. 4, 1986

[87] PCT Pub. No.: WO86/06093

PCT Pub. Date: Oct. 23, 1986

[30] Foreign Application Priority Data

Apr. 9, 1985 [AT] Austria .................... 1068/85

[51] Int. Cl.⁴ .................................................. C12C 1/00
[52] U.S. Cl. ........................................ 435/306; 435/162; 435/304; 426/494; 202/173
[58] Field of Search ................. 202/173, 238, 264; 203/19, 20, DIG. 13; 426/493, 494; 435/302-306, 286, 161, 162, 312, 316

[56] References Cited

U.S. PATENT DOCUMENTS

| | | | |
|---|---|---|---|
| 3,816,266 | 6/1974 | Izumi et al. | 202/173 |
| 4,009,075 | 2/1977 | Hoge | 435/162 |
| 4,347,321 | 8/1982 | Lionelle et al. | 203/DIG. 13 |
| 4,359,533 | 11/1982 | Wilke et al. | |

FOREIGN PATENT DOCUMENTS

| | | |
|---|---|---|
| 0039518 | 11/1981 | European Pat. Off. . |
| 1563514 | 4/1969 | France . |
| 376089 | 5/1964 | Switzerland . |
| 443226 | 1/1968 | Switzerland . |

*Primary Examiner*—Samuel Scott
*Assistant Examiner*—Noah Kamen
*Attorney, Agent, or Firm*—Cushman, Darby & Cushman

[57] ABSTRACT

Apparatus for continously producing ethanol from fermentable sugar solutions comprises horizontal, tubular mixing and separating vessel having internal rotating plates inclined relative to the horizontal axis of rotation. The yeast charged to the vessel is extracted from the vessel and is subjected to a multi-stage fermentation within horizontal fermentation vessels. Within the fermentation vessels there are again arranged inclined rotating plates. The ethanol is separated in a gaseous phase, the pressure being reduced stepwise in succeeding fermentation vessels tubes.

5 Claims, 3 Drawing Sheets

APPARATUS FOR CONTINUOUSLY RECOVERING ETHANOL FROM FERMENTABLE SUGAR SOLUTIONS

The invention relates to apparatus for continuously recovering ethanol from fermentable sugar solutions, the apparatus comprising means for mixing sugar solution with yeast and for separating yeast charged with sugar solution and further comprising a fermentation container adapted for being subjected to sub-atmospheric pressure.

BACKGROUND OF THE INVENTION

From No. EP-A-44 428 it is known to produce by comminuting, thermal digestion and saccharification of starch-containing raw materials a mash for producing alcohol from starch or starch-containing raw materials. There is known a number of sugar containing raw materials from which can directly be obtained sugar solutions by extraction, and it is known to degrade such sugar solutions down to glucose and to subject a mash obtained in this manner to fermentation. The fermentation process requires different conditions, depending on the composition of the raw materials and of the mash, and it requires a relatively long reaction time for completion. It is a drawback of known fermentation processes that the mashes and fermentable substrates contain the fermentable sugar as well as the fermentation products in concentrations changing during the fermentation, which adversely influence the reaction speed or fermentation speed.

BRIEF DESCRIPTION OF THE INVENTION

The present invention aims at providing an apparatus which achieves in a simple manner the application of sub-atmospheric pressure and the separation of the alcohol by distillation without excessive foam formation. The apparatus includes a fermentation assembly which is formed of a plurality of horizontal tubular vessels adapted for being connectable to each other via pressure locks, in particular via valves or pumps, the individual tubular vessels comprising internal plates which are rotatable around the horizontal axis of the vessel and which are at least partially immersed in the fermentation substrate. The plates are inclined with respect to the horizontal axis at an angle of greater or smaller than 90°. The tubular vessels comprise separate gas discharge conduits. On account of the fermentation container being subdivided into a plurality of individual tubular vessels, a different atmosphere and, above all, a different pressure can be maintained within the various vessels. On account of the preferred procedure, according to which the fermentation is performed under sub-atmospheric pressure, an increased foam formation must be expected. Such foam formed during the fermentation can, in a simple manner, be destroyed or be prevented from being formed if the individual vessels comprise plates which are rotatable around the container axes and entail upward and downward movement and reciprocating movement of the liquid phase. For this purpose, the plates are oriented relative to the axis of rotation such that they include with said axis an angle of more or less than 90°, whereby a pulsating hydrostatic pressure is generated which provokes degassing without foam formation. On account of the individual vessels being connected one with the other via pressure locks, a different pressure can be maintained in the different vessels, and in a preferred mode of operation the pressure is reduced stepwise during the process.

An analogous horizontal tubular vessel comprising internal rotatably supported plates can be arranged upstream of the fermentation vessels as a mixing and separating means. The plates are rotatable around the axis of the respective vessel in common with the vessel or separately therefrom, and they engage the inner circumference of the vessel in a substantially tight manner. Also, the plates are alternately oppositely inclined relative to said axis and have one flow passage located close to the inner circumference of the vessel and at least one flow passage located close to the axis. The two flow passages in adjacent plates are, as viewed in axial direction, staggered 180° in the sense of rotation. The vessel has at one end a supply opening for yeast and optionally for sugar solution and a discharge opening for depleted sugar solution or for charged yeast sludge. At the other end there are an optional supply opening for sugar solution and a discharge opening for charged yeast sludge or for depleted sugar solution. Separation of the floating phase from the remaining phase depleted of sugar is in this case effected on account of the fact that the floating phase flows via the passages located close to the axis into an adjacent chamber when this chamber has, on account of the geometry of the position of the plates, a lower liquid level. On account of the substantially tight engagement of the internal wall of the vessel by the plates, transport of the medium always occurs from a chamber having a higher liquid level into a chamber having a lower liquid level, the height of the liquid level being dependent on the distance between adjacent plates within the lower portion of the vessel. Inversely, transport of the other phase in the opposite direction is effected on account of the fact that each plate has flow passages located near the axis and located at a greater distance from the axis and staggered 180° in adjacent plates. Thus, a flow passage located in proximity of the axis and a flow passage located at a greater distance from the axis of a given plate is moved below the liquid level during one revolution of the plate, so that overflow into the adjacent chamber which has a correspondingly lower liquid level is achieved. On account of the liquid level being cyclically raised and lowered, there results from the staggered arrangement of these flow passages a transport in one direction of the phase located in proximity of the axis and a transport of the phase located at a greater distance from the axis in the other direction.

Simultaneously, with a good mixing effect and a good charging of the yeast with sugar to be subjected to fermentation, such an apparatus provides the possibility to separate the yeast charged with sugar from the depleted sugar solution.

The apparatus according to the invention is in an advantageous manner further constructed such that the fermentation vessels have the supply openings and discharge openings for charged yeast located close to the opposite front sides of the vessels and such that the plates have flow passages for the transport of the fermentation substrate from the supply opening to the discharge opening. If movement of the plates shall directly be utilized for transporting the liquid phase from the supply opening to the discharge opening, a substantially tight engagement with the inner surface of the vessel is required for the purpose of obtaining different liquid levels between adjacent chambers. The flow passages can, however, also be formed of annular gaps between the outer contour of the plates and the inner surfaces of the vessels, if there are provided external means for producing a directional movement. If in accordance with a preferred further construction, a procedure is selected such that the pressure in subsequent vessels can be lowered in a stepwise manner, the suction pressure of the succeeding fermentation vessel can be utilized for removing the medium from the preceeding fermentation vessel, so that the directional flow can be obtained on account of the differing pressure. In a particularly advantageous manner, the operation is effected in at least three stages by connecting in series three vessels tubular containers, the pressure within the first vessel preferably being between 0.75 and 0.95 bar absolute, in the second vessel being beween approximately 0.25 to 0.50 bar absolute and within the third vessel 0.1 to 0.25 bar absolute. In this manner there can be removed from the first vessel, within which the fermentation is started, essentially steam, carbon dioxide and already traces of alcohol. When lowering the pressure to that of the second vessel there can be extracted vapors enriched in alcohol, whereas from the third vessel there can be extracted substantially pure ethanol until there is obtained an admissible residual content of alcohol. Such proceeding in a plurality of stages provides the advantage that the products obtained have a higher purity.

After the end of the fermentation, yeast can be extracted from the vessel subjected to the lowest pressure, the yeast being extracted from the vessel being subjected to the lowest pressure can at least partially, optionally via a conditioning stage, be returned to the mixing and separating means.

DETAILED DESCRIPTION

Figure 1:
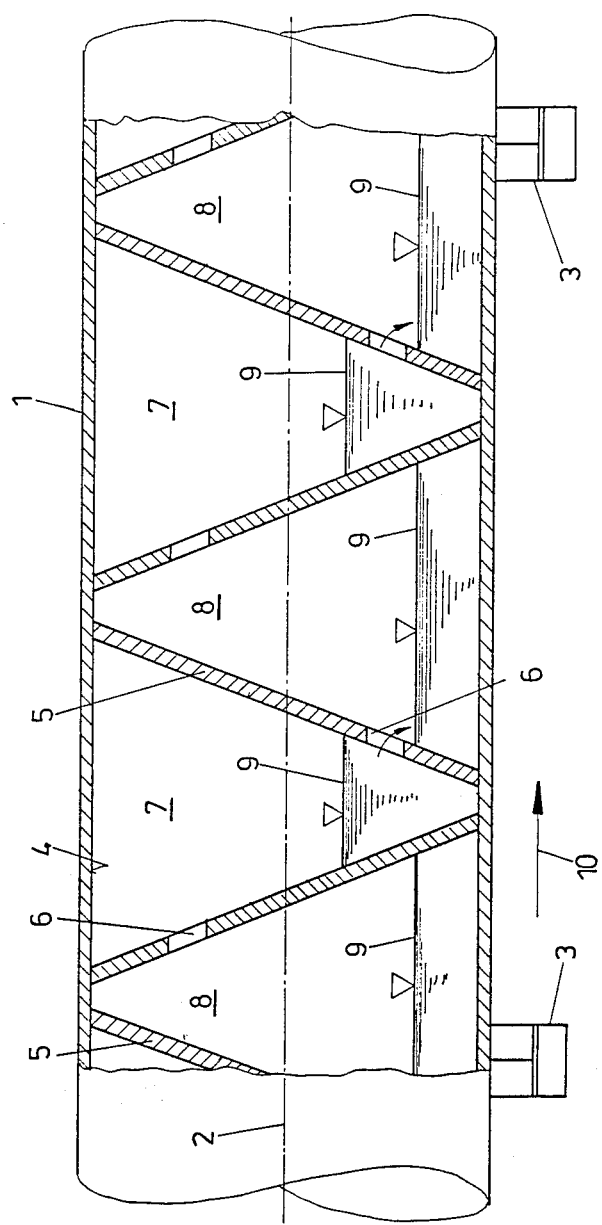
FIG. 1 is a schematic axial section through a first embodiment of a fermentation vessel.

FIG. 1 shows a horizontal tubular fermentation vessel supported on bearings 3 for rotation around its axis 2. The inner surface 4 of the vessel is connected with plates or discs 5 which are alternately oppositely inclined one relative to the other. Each of these plates 5 has in proximity to its circumference a perforation 6, the perforations 6 being, as seen in direction of the axis 2, offset one relative to the other for an angle of 180°. Chambers 7 and 8 are formed between the adjacent plates 5. Within the chambers 7 the liquid level 9 rises on account of the position assumed by adjacent plates 5, whereas the liquid level within the chambers 8 sinks on account of the position assumed by adjacent plates 5, whereas the liquid level within the chambers 8 sinks on account of the enlarged lower portions of these chambers. The difference in hydrostatic pressure can be utilized for transporting purposes between adjacent chambers 7 and 8 when the perforations 6 are immersed below the liquid level, and the result is a directional flow in direction of the arrow 10.

Figure 2:
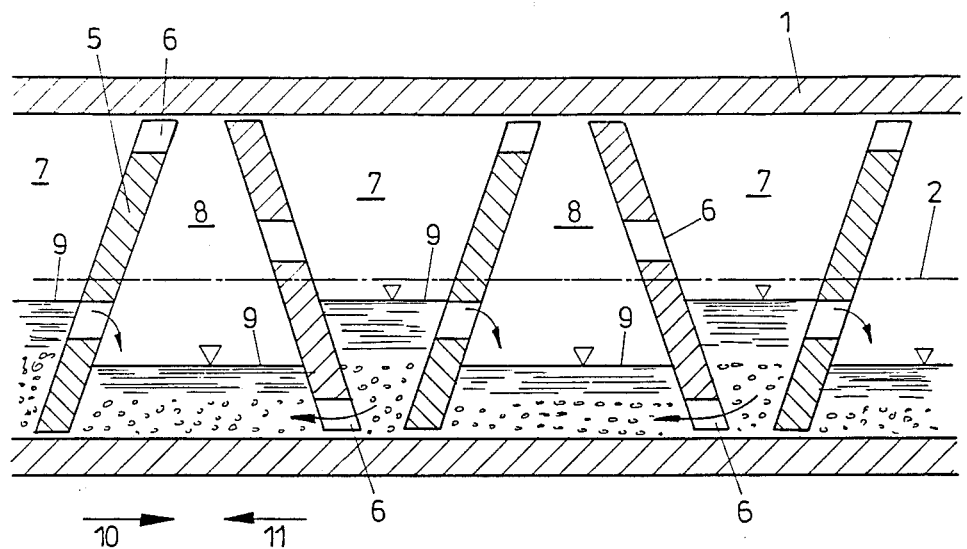
FIG. 2 is a schematic axial section of a mixing and separating vessel.

In the embodiment of a horizontal, tubular mixing and separating vessel according to FIG. 2, each plate 5 has relative to the common axis 2 of rotation two perforations 6 at locations of the plate 5 which are opposite one relative to the other with reference to the axis 2. Both perforations 6 of one plate are thus 180° staggered one relative to the other, with respect to one revolution around the axis 2. When the perforations 6 located in proximity of the axis are immersed into the medium, the medium flows in direction of the arrow 10 between one chamber 7 and one chamber 8. Immersion of the perforations 6 which are located at a greater distance from the axis results in an opposite flow direction in direction of the arrow 11. The plates can be rigidly connected with the tube 1, or the plates can be mounted on a common rotating axis. In the latter case there is provided a space between the wall of the vessel and the periphery of each plate to permit rotation of the plates relative to the vessel, and this results to a certain degree in an alternating flow direction between adjacent chambers 7 and 8. If the cross section of each space is sufficiently small, the liquid level is still lifted for a considerable degree, so that a directional transport of two phases in opposite directions results. The phase of lower specific gravity, such as for example floating sludge or foam, is transported in direction of the arrow 10 on account of the perforations 6 being located in proximity of the axis, whereas the phase of the higher specific gravity is transported adjacent the surface of the vessel in the opposite direction, indicated by the arrow 11. Both front ends of the vessel 1 can be tightly closed and be provided with supply openings and discharge openings not shown. In FIG. 2, the discharge opening for the phase of higher specific gravity is provided at the left end of the vessel, and the discharge opening for the phase of lower specific gravity, in particular foam or floating sludge, is provided at the right end.

Figure 3:
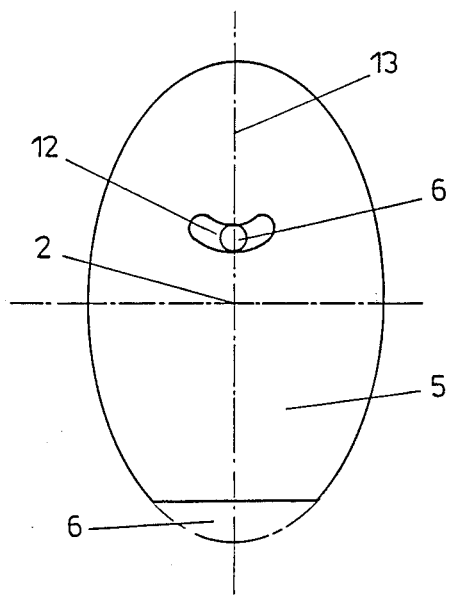
FIG. 3 is a top plan view of a plate for the mixing vessel of FIG. 2.

The individual plates in FIG. 2 have the substantially elliptical shape shown in FIG. 3. The perforations 6 located at a greater distance from the axis are formed by cut-off segments, and the perforations 6 located in proximity of the axis are formed by bores such as elongated holes 12. In each plate the two perforations 6 are advantageously symmetrically arranged relative to the main axis 13 of the elliptical shape of the plate.

Figure 4:
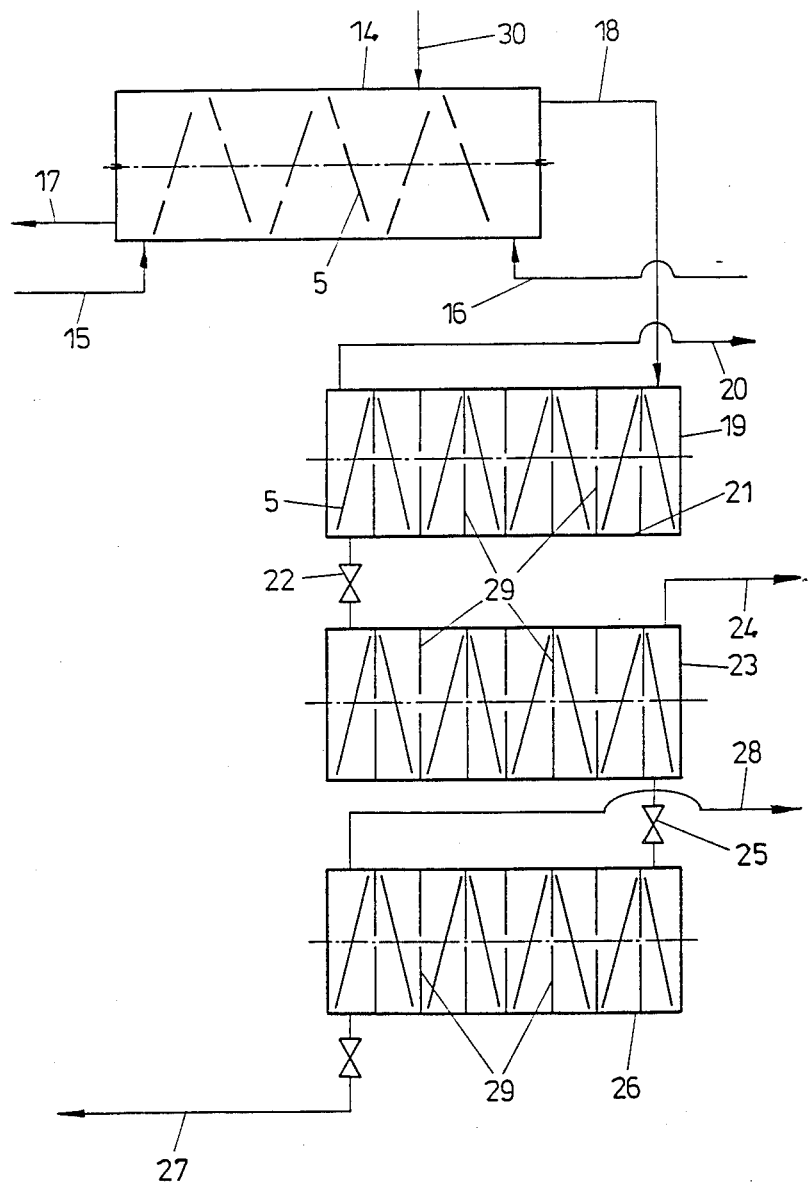
FIG. 4 is a schematic view of an apparatus, composed of the components shown in FIGS. 1 and 2, for producing alcohol from fermentable substrates.

In the schematic representation according to FIG. 4, a mixing and separating vessel corresponding to FIG. 2 is designated by 14. A supply conduit 15 for non-charged yeast and a further supply conduit 16 for a solution rich in sugar open into the vessel 14. There is further provided a discharge conduit 17 for depleted sugar solution and a discharge conduit 18 for the flotate, in particular the yeast. On account of the flow conditions explained in detail in connection with FIGS. 2 and 3, there can be achieved, simultaneously with an intense mixing of the solution rich in sugar and the yeast, a separation of the floating yeast from the sugar solution. The charged yeast now enters via a conduit 18 a first horizontal tubular fermentation vessel 19, which is subjected to a pressure of approximately 0.8 bar absolute via a gas conduit 20. The plates 5, which are rotatably supported within fermentation the vessel 19, are shown without flow passages in this schematic view. There exists, however, between the inner surface 21 of the vessel 19 and the circumference of the plates 5 a gap which is sufficient to generate a directional flow, for example by applying a suction pressure at the end of the vessel 19 which is located opposite the supply means. For this purpose, the vessel 19 is connected with a second, subsequent fermentation vessel 23 via a shut-off valve or a throttle valve 22, the second vessel 23 being subjected to a lower pressure than that existing within the vessel 19 via a gas exhaust conduit 24. The pressure within the second vessel 23 is, for example, selected in the order of 0.3 bar absolute. Finally, the liquid medium extracted from the opposite side enters via a shut-off valve or a throttle valve 25 the subsequent third fermentation vessel 26. After the fermentation has been completed, the yeast can be extracted via a conduit 27 and at least partially be returned via the conduit 15 to the mixing and separating vessel 14.

The third fermentation vessel 26 is, for example, subjected to a pressure of approximately 0.15 bar absolute, so that substantially pure alcohol can be extracted from this vessel 26. For this purpose, a gas discharge conduit 28 is provided.

The individual fermentation vessels can without difficulty also be provided with rotating plates 5 having no passages or perforations as is shown in FIG. 4. In these cases there are provided rigid intermediate plates 29. The portion of each plate 29 near the axis has a flow passage encircling the axis such that there remains an annular gap around the axis.

A supply conduit for flocculating agent is schematically designated by 30.

What is claimed is:

1. Apparatus for continuously recovering ethanol from fermentable sugar solutions, comprising means for mixing sugar solution with yeast and for separating yeast charged with sugar solution, said apparatus further comprising at least first and second horizontal tubular fermentation vessels, the first vessel having a fermentation substrate inlet connected to said mixing and separating means for receiving separated yeast and sugar and a fermentation substrate outlet connected to an inlet to the second vessel through a pressure lock and each vessel having an ethanol vapor discharge outlet connectable to a source of subatmospheric pressure, and each vessel having internal plates which are rotatable around the horizontal axis of the respective vessel and located so as to be at least partially immersible in fermentation substrate in the vessel, said plates being inclined with respect to said axis at greater or smaller than 90°.

2. Apparatus as in claim 1 wherein the mixing and separating means includes a horizontal tubular vessel and a plurality of axially spaced apart internal rotatable plates which are rotatable around the horizontal axis of said mixing and separating vessel, alternate plates being inclined in opposite directions relative to said axis, each plate having a first flow passage located near the inner circumference of the vessel and a second flow passage located near said axis and the first and second flow passages of adjacent places being 180° offset with respect to each other about said axis, said vessel having a first end fitted with a supply opening for yeast and with a discharge opening for depleted sugar solution and an opposite end fitted with a discharge opening for yeast.

3. Apparatus as in claim 1 wherein each fermentation vessel has opposite ends, the fermentation substrate inlet of each vessel being located near one end and the fermentation substrate outlet being located near the opposite end, and wherein the internal rotatable plates have flow passages for the transport of fermentation substrate from the inlet to the outlet of each fermentation vessel.

4. Apparatus as in claim 1 including means for reducing the pressure in the second fermentation vessel to a lower value than the pressure in the first fermentation vessel.

5. Apparatus as in claim 4 including means for returning fermentation substrate from the fermentation vessel of lowest internal pressure to the mixing and separating means.